United States Patent [19]

Faletti et al.

[11] 3,969,390

[45] July 13, 1976

[54] CATALYTIC PROCESS FOR PREPARING UNSATURATED NITRILES FROM OLEFINS, AMMONIA AND OXYGEN

[75] Inventors: Franco Faletti; Nicola Giordano; Paolo Marinozzi; Joannes Bart, all of Milan; Arsenio Castellan, Bollate (Milan), all of Italy

[73] Assignee: Montedison S.p.A., Milan, Italy

[22] Filed: Jan. 10, 1975

[21] Appl. No.: 540,165

[30] Foreign Application Priority Data

Jan. 11, 1974  Italy ................................. 19334/74

[52] U.S. Cl. .............................. 260/465.3; 252/439
[51] Int. Cl.² .................................... C07C 120/14
[58] Field of Search ............................... 260/465.3

[56] References Cited
UNITED STATES PATENTS

| | | | |
|---|---|---|---|
| 3,226,421 | 12/1965 | Giordano et al. ................ | 260/465.3 |
| 3,347,899 | 10/1967 | Caporali et al. ................. | 260/465.3 |
| 3,471,545 | 10/1969 | Giordano et al. ................ | 260/465.3 |
| 3,625,867 | 12/1971 | Yoshino et al. ............... | 260/465.3 X |
| 3,641,102 | 2/1972 | Reulet et al. .................... | 260/465.3 |
| 3,803,207 | 4/1974 | Tellier et al. .................... | 260/465.3 |

*Primary Examiner*—Joseph Paul Brust

[57] ABSTRACT

Alpha, beta unsaturated nitriles are prepared from olefins by reaction thereof with ammonia and oxygen, in the gas phase and in the presence of a novel catalyst system consisting of the elements cerium, tellurium, molybdenum, of at least one of the elements selected from the group comprising iron, chromium and aluminium, and moreover of oxygen chemically combined with the above cited elements.

4 Claims, No Drawings

CATALYTIC PROCESS FOR PREPARING UNSATURATED NITRILES FROM OLEFINS, AMMONIA AND OXYGEN

THE PRIOR ART

It is known to prepare alpha, beta unsaturated nitriles from olefins, ammonia and oxygen and in particular to prepare acrylonitrile from propene, ammonia and oxygen, using catalysts of different kinds.

For instance, British patent No. 1,016,031 discloses a catalyst consisting of molybdenum, tellurium, cerium and oxygen for use in preparing alpha, beta-unsaturated nitriles from olefins ammonia and oxygen.

United States Pat. No. 3,262,962 discloses a catalyst of the formula $Mo_{12}Ce_1$ and in addition Bi. However the catalysts of the prior art have the drawbacks that the conversion of ammonia is not high and furthermore they need a remarkable excess of oxygen in the reaction mixture.

THE PRESENT INVENTION

One object of this invention is to provide an improved process for the catalyst ammoxidation of olefins to high yields of alpha, beta-unsaturated nitriles.

Another object is to provide new catalysts which afford high activity in the preparation of unsaturated nitriles and moreover other considerable advantages that essentially contribute to an efficient and economic operation of the process according to the present invention.

It is possible, therefore, to employ low air/olefins ratios and to obtain high volume-time yields (high hourly weight-volume velocities). The catalyst exhibits an extraordinarily efficient utilization of the ammonia, wherefore the unconverted $NH_3$ amounts present in the effluents from the reactor are substantially reduced and the amounts of sulphuric acid necessary to neutralize said ammonia are minimized too. This brings about an improvement in the operation of the recovery section and an improvement with regard to fouling, resulting from a reduction in the formation of by-products subject to being polymerized.

A furhter important advantage achieved with the catalyst according to this invention consists in the low costs of the essential catalyst components and in the easiness of preparation.

Another advantage is the exceptional stability in the long run of the catalysts containing iron and/or chromium and/or aluminum, cerium, tellurium and molybdenum.

The oxidation catalysts, already known from the literature, are very often characterized, during their employment under reaction conditions, by a worsening of the morphological characteristics and of the values concerning catalytic activity and selectivity for nitriles.

The present invention provides a system which is very stable under the reaction conditions, as shown by the activity and selectivity values, which are particularly high not only after the first reaction hours, but remain such for an unlimited period of time.

The reagents employed for producing unsaturated nitriles according to the present invention comprise: oxygen, ammonia and propylene or isobutene.

The olefin may be in admixture with paraffinic hydrocarbons such as, for example, ethane, propane, butane and pentane and, for instance, the starting substance may be a propylene and propane mixture. Consequently it is possible to utilize a usual refining product without any special separation of the olefin.

According to a preferred embodiment, the process of this invention is characterized in that a mixture consisting of propylene, ammonia and oxygen is contacted with the catalyst at high temperature and at atmospheric pressure, or at a pressure near atmospheric.

The process according to this invention may employ any suitable source of oxygen. However, for economic reasons, it is preferable to use air as oxygen source. From a strictly technical view point, pure molecular oxygen yields equivalent results.

The oxygen/olefin molar ratio in the starting material introduced into the reactor ranges from 1.5:1 to 3.5:1, a ratio of about 2:1 to 2.8:1 being preferred.

The ammonia/olefin molar ratio of the feed may vary from about 0.8:1 to 2:1. There is no real upper limit for the ammonia/olefin ratio, but generally there is no reason for exceeding a ratio of 1.5:1.

With ammonia/olefin ratios substantially lower than the stoichiometric ratio 1:1, only negligible amounts of the olefin oxygenated derivatives form, while the selectivity for acrylonitrile remains remarkably high.

Surprisingly, within the range indicated for the ammonia/olefin ratio it is possible to attain a maximum utilization of ammonia, which is highly desirable.

It has been now found that the reaction selectivity and the nitrile yield are so high, that it is of no advantage to add steam to the mixture fed to the reactor.

The reaction is conducted at a temperature comprised between about 350° and about 550°C, the preferred temperature being comprised between about 400° and about 500°C.

The total pressure at which the reaction is conducted is not particularly important and therefore it may vary within wide limits, but it depends in part on economic factors: Therefore, the process is generally operated at a pressure close to atmospheric pressure and, more precisely, at a pressure slightly higher, i.e. comprised between 1 and 5 absolute atmospheres.

The contact time, expressed in seconds as the ratio between catalytic bed volume and the volumes per second of fed gaseous mixtures of the reagents, measured under the average conditions of temperature and pressure existing in the catalytic bed, may vary depending on the temperature and as a function of the nature of the catalyst, of the nature of the catalytic bed, fixed or fluidized, and of the catalyst size; generally it may range from 0.1 to 20 seconds; a preferred range is 1–15 seconds because that range corresponds to the most usual practical operating conditions.

For practising the process according to this invention it is possible to use, in general, any apparatus suitable for carrying out oxidation reactions in the vapor phase.

The process according to this invention may be conducted either continuously or discontinuously, but, for practising it on a large technical sacle, the continuous method is preferred.

The process forming the object of this invention may be practised by using the catalyst in the form of fixed or fluidized bed; in the latter case which, as is known, offers some advantages as regards the thermal control of the reaction, the nature of the support and the preparation method for obtaining a microspheroidal catalyst having a suitable granulometric distribution become particularly important. The reagents may be fed onto the catalyst already preheated at a temperature almost equal to the reaction temperature or at room temperature, in such case they rapidly heat in contact with the catalytic bed, no matter whether fixed or fluidized. The reagents may be fed onto the catalyst already throughly premixed or partly premixed or thoroughly separated; the feeding of the separated or partially premixed reagents can be generally carried out more easily in a fluidized bed reactor.

It is also known and possible to feed the whole air amount and part of the olefin and/or of the ammonia to the reactor bottom and then to feed the remaining amounts of olefin and/or ammonia to one or more upper points inside the catalytic bed.

When the process according to the present invention is practised with a catalytic fluidized bed reactor, it may be particularly convenient to operate according to British Pat. No. 1,181,292. When conducting the reaction according to the catalytic fixed bed technique, said bed can be realized, according to the art, by arranging the catalyst inside the tubes of a tube bundle reactor and by removing the reaction heat by circulating suitable fluids outside the tubes and, for instance, more usually by means of mixtures of molten salts. It is possible also to operate in a reactor consisting of more adiabatic reaction stages alternated with cooling zones of the reacting mixture.

The catalyst may be also periodically regenerated or reactivated, and this can be achieved, for instance, by bringing the catalyst at high temperature into contact with the air.

The regeneration of the catalyst object of the present invention, though possible from a technical viewpoint, is generally not necessary, as the oxygen present under the reaction conditions is sufficient to keep the catalyst in the best oxidation state.

The reaction products can be recovered according to any of the known methods. One of such methods consists of the following operations: the gases flowing out from the reactor are scrubbed with cold water or with a suitable solvent to remove the reaction products. According to a preferred case, it is possible to use acidified water to absorb the reaction products and to neutralize the small amount of unreacted ammonia. The final step for recovering the product can be conducted in the usual ways.

The catalyst employable in the process according to this invention is a mixture, a composition or possibly a complex of the oxides of Ce, Te, Mo, Fe and/or Cr and/or Al.

Said elements are present in the catalytic composition in such amounts that the atomic ratios to one another correspond to the following formula:

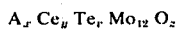
$$A_x Ce_y Te_v Mo_{12} O_z$$

wherein:
A may be Fe and/or Cr and/or Al
$x$ is a number comprised between 0.3 and 4.0
$y$ is a number comprised between 1.0 and 10.0
$v$ is a number comprised between 1.0 and 10.0
$z$ is a number taken to satisfy the average valences of the elements in the oxidation stages in which they exist in the catalyst.

The catalytic composition may be used without carrier and, as such, it exhibits an excellent catalytic activity. For practical uses it is preferably employed in combination with a carrier, as carrier being utilizable any material suited to the purpose such as, for instance, silica, alumina, silicium carbide, silica-alumina, phosphates, silicates, borates, carbonates, provided they are stable under the reaction conditions they will be subjected to during the use of the catalyst. The preferred carrier is silica. The amount of active catalytic composition in relation to the carrier's weight may vary over wide range, according to the characteristics of the carrier and to the preparation method, but in any case it is profitable to operate with an active catalytic composition amount lower than 50% by weight; this permits to obtain little expensive catalysts having an excellent catalytic activity.

The employment of the catalysts of the present invention permits the attainment of high acrylonitrile yields and a very high propylene and ammonia conversion, up to 100%.

Particularly useful is the almost thorough conversion of the fed ammonia, that permits the reduction to zero of the sulphuric acid consumption and, in consequence, the formation of the by-product ammonium sulphate, without jeopardizing the acrylonitrile yields, which remain very high.

Furthermore, it is particularly surprising that these exceptional activities remain unchanged in the long-run; the same may be said also for the morphological and redox characteristics of the catalysts, as proved by the surface area values and by any other data determined for that purpose. These results are to be ascribed to the fact that the catalysts according to the present invention promote a regular oxidation process easily controllable as regards reaction temperature and contact times.

For preparing the catalyst, it is possible to use all the proper methods already known to those skilled in the art. Suitable methods of preparing a supported catalyst to be employed in the form of microspheroidal particles in a catalytic fluidized bed reactor are, in particular, those described in British Pat. Nos. 1,174,786 and 1,167,530.

Various starting compounds may be used for preparing the catalytic composition according to this invention. Thus, for instance, the starting molybdenum compounds may be selected- depending upon the catalyst preparation method - from amongst: ammonia molybdates, molybdic acid, molybdic anhydride, ammonium salt of the molybdic-ceric acid and iron, chromium and aluminium molybdate. For iron, chromium and aluminum it is possible to use the nitrate, the oxide, their organic salts and, optionally, also the metals and the molybdates. As cerium compounds it is possible to use the nitrate, molybdenum-ceric acid or its ammonium salt. Tellurium may be introduced into the catalyst in the form of oxide, or telluric acid, or also as the metal in powder form. The catalyst can be prepared according to the known methods of the art, for example those described in British patents Nos. 1,016,031 and 1,167,530.

All the preparation methods entail a final activation step of the catalytic composition, consisting in a heating treatment in the presence of air at a temperature ranging from 450° to 700°C, preferably from 500° to 650°C, in any case higher than the employment temperature.

Some proper methods of preparing the catalyst are indicated hereinafter:
1. An aqueous solution of the ammonium salt of the cerium-molybdic acid is mixed with a nitric solution of TeO$_2$, of iron and/or chromium and/or aluminium, nitrate and, optionally, of cerium nitrate and an aerogel of the commercial type. After evaporation, the catalyst is extruded, dried and activated at a temperature comprised between 400° and 600°C.

2. A nitric solution of telluric acid and nitrates of Ce and iron and/or chromium and/or aluminium is added with a silica sol and then with an aqueous solution of ammonium paramolybdate. The mixture resulting therefrom is spray-dried and the catalyst thus obtained in the form of particles is activated by heating at a temperature between 400° and 600°C.

3. An aqueous solution of ammonium paramolybdate is admixed to a nitric solution of telluric acid and nitrates of cerium and iron and/or chromium and/or aluminium. The solution resulting therefrom, having a volume equal to that of the carrier's pores, is used to impregnate a silica of the commercial type, optionally of microspheroidal size. The product obtained in dried for 12 hours at 110°–120°C and then activated at a temperature ranging from 400° to 600°C. Besides being used for impregnating the silica, the resulting solution can be evaporated to dryness, the residue can be ground and activated, thus obtaining a non-supported catalyst.

4. An aqueous solution of ammonium paramolybdate is added, under intense stirring, with metal tellurium in powder form and then gradually with $H_2O_2$ under hot conditions. Subsequently, a further amount of $H_2O_2$ is admixed under cold conditions, then $HNO_3$ and the nitrates of cerium and of iron and/or chromium and/or aluminium. The solution thus obtained, once suitably diluted with water, is used to impregnate a silica of the commercial type according to the modalities described hereinbefore. The product is dired and activated.

5. Ammonium paramolybdate is dissolved in an aqueous solution of $H_2O_2$, thus obtaining an ammonium permolybdate aqueous solution. Separately, another solution acidified by $HNO_3$ is prepared by dissolving telluric acid $H_2TeO_4 \cdot 2H_2O$, iron and/or chromium and/or aluminium nitrate and cerium nitrate. The permolybdate solution is then gradually poured into the one containing tellurium, cerium, iron and/or chromium and/or aluminium. The solution obtained, once suitably diluted, is used to impregnate a silica of the commerical type. The product is then dried and activated.

The following examples are given to better illustrate some practical embodiments of the present invention, without being however a limitation thereof.

EXAMPLE 1

The catalyst was prepared according to the method 5) described hereinbefore and resulted to be composed for 76.1% by a $SiO_2$ carrier and for 23.9% by an activated part in which the atomic ratios of the elements are represented by the empirical formula $$Cr_2 \; Ce_3 \; Te_4 \; Mo_{12}$$

The ammoxidation reaction was conducted in a reactor charged with aforesaid catalyst, in the form of fixed bed. The feeding mixture was made up of propylene, $NH_3$, air in the following molar ratios: 1/1.5/12. The reaction temperature was 440°C and the contact time 2.5 seconds.

On the basis of the analysis of the reaction gases, an acrylonitrile yield of 84.3% was calculated, by yield meaning the following ratio:

$$\frac{\text{grams of carbon of the acrylonitrile obtained}}{\text{grams of carbon of the propylene fed}} \times 100$$

The propylene conversion was 97.2%, by conversion meaning the ratio between the amount of reacted propylene and the amount of fed propylene. The ammonia conversion, determined by titration, was 96.4%. The selectivity for acrylonitrile was 86.8%. whenever used herein, the term "selectivity" means the ratio:

$$\frac{\text{obtained grams of carbon of the product considered}}{\text{grams of carbon of the reacted propylene}} \times 100.$$

EXAMPLE 2

The catalyst was prepared according to method 4 hereinabove and was composed for about 75% of a $SiO_2$ carrier and for the rest of the activated part, in which the atomic ratios of the elements to one another are indicated by the empirical formula $$Cr_1 \; Ce_4 \; Te_4 \; Mo_{12}$$

The ammoxidation reaction was conducted in a reactor charged with the abovesaid catalyst in the form of fixed bed. The feeding mixture was made up of propylene, ammonia, air in the following molar ratios: 1/1.3/11. The reaction temperature was 440°C and the contact time 2.5 seconds.

On the basis of the analysis of the reaction gases, an acrylonitrile yield of 82.0% and an ammonia conversion of 97.9% were calculated.

EXAMPLE 3

The catalyst was prepared according to method 5 hereinabove and was composed for 74.6% of a $SiO_2$ carrier and for the rest of the activated part in which the atomic ratios of the elements to one another are indicated by the empirical formula $$Cr_3 \; Ce_7 \; Te_4 \; Mo_{12}$$

The ammoxidation reaction was conducted in a reactor charged with catalyst in the form of fixed bed. The feeding mixture was made up of propylene, ammonia, air in the following molar ratios: 1/1.3/12. The reaction temperature was 420°C and the contact time 4 seconds.

On the basis of the analysis of the reaction gases, an acrylonitrile yield of 81.3% was calculated. The propylene conversion was 97.3% and that of ammonia was 99.2%.

EXAMPLE 4

The catalyst was prepared according to method 3 hereinabove and was composed for about 65% of a $SiO_2$ carrier and for the rest of an activated part in which the atomic ratios of the elements to one another are indicated by the empirical formula $$Fe_4 \; Ce_4 \; Te_2 \; Mo_{12}$$

The ammoxidation reaction was conducted in a reactor charged with said catalyst, in the form of fixed bed. The feeding mixture was made up of propylene, ammonia, air in the following molar ratios: 1/1.5/11. The reaction temperature was 460°C and the contact time 1.5 seconds.

On the basis of the analysis of the reaction gases, an acrylonitrile yield of 79.7% and an ammonia conversion of 100% were calculated.

EXAMPLE 5

The catalyst was prepared according to method 4 hereinabove and was composed for about 75% of a SiO$_2$ carrier and for the rest of the activated part, in which the atomic ratios of the elements to one another are indicated by the empirical formula $Fe_1 Ce_4 Te_6 Mo_{12}$ The ammoxidation reaction was conducted in a reactor charged with said catalyst, in the form of fixed bed. The feeding mixture was made up of propylene, ammonia, air in the following molar ratios: 1/1.5/12. The reaction temperature was 440°C and the contact time 2.5 seconds.

On the basis of the analysis of the reaction gases, an acrylonitrile yield of 76.6% and an ammonia conversion equal to 99.0% were calculated.

EXAMPLE 6

The catalyst was prepared according to method 5 hereinabove and was composed for about 75.5% of a SiO$_2$ carrier and for the rest of the activated part in which the atomic ratios of the elements to one another are indicated by the empirical formula $Al_{0.95} Ce_5 Te_4 Mo_{12}$ The ammoxidation reaction was conducted in a reactor charged with said catalyst, in the form of fixed bed. The feeding mixture was made up of propylene, ammonia, air in the following molar ratios: 1/0.95/11. The reaction temperature was 440°C and the contact time 2.5 seconds.

On the basis of the analysis of the reaction gases, an acrylonitrile yield of 80.2% and a propylene conversion equal to 97.4% were calculated.

EXAMPLE 7

The catalyst was prepared according to method 2 hereinabove and was composed for about 65% of a SiO$_2$ carrier and for the rest of the activated part, in which the atomic ratios of the elements are indicated by the empirical formula $Al_{2.7} Ce_{1.4} Te_5 Mo_{12}$ The ammoxidation reaction was conducted in a reactor charged with said catalyst, in the form of fixed bed. The feeding mixture was made up of propylene, ammonia, air in the following molar ratios; 1/0.95/11. The reaction temperature was 430°C and the contact time 3.5 seconds.

On the basis of the analysis of the reaction gases, an acrylonitrile yield of 79.8%, a propylene conversion of 99.2% and an ammonia conversion of 100% were calculated.

EXAMPLE 8

The catalyst was prepared according to method 4 hereinabove and was composed for about 70% of a SiO$_2$ carrier and for the rest of the activated part in which the atomic ratios of the elements are indicated by the empirical formula $Al_3 Ce_5 Te_8 Mo_{12}$ The ammoxidation reaction was conducted in a reactor charged with abovesaid catalyst, in the form of fixed bed. The feeding mixture was made up of propylene, ammonia, air in the following molar ratios: 1/0.95/11. The reaction temperature was 420°C and the contact time 4.5 seconds.

On the basis of the analysis of the reaction gases, an acrylonitrile yield of 80.2%, a propylene conversion of 98.5% and an ammonia conversion of 100% were calculated.

EXAMPLE 9

The catalyst was prepared according to method 4 hereinabove and was composed for about 74% of a SiO$_2$ carrier and for the rest of the activated part, in which the atomic ratios of the elements are indicated by the empirical formula $Al_{2.3} Ce_5 Te_4 Mo_{12}$ The ammoxidation reaction was conducted in a reactor charged with said catalyst, in the form of fluidized bed. The pressure in the reactor was 1.8 kg/cm$^2$ abs. The feeding mixture was made up of propylene, ammonia, air in the following molar ratios: 1/0.90/12. The reaction temperature was 440°C and the contact time 12 seconds. The test was conducted for more than 600 hours without any interruption, the results being very constant.

On the basis of the gas-chromatographic analysis of the effluent gases carried out after a 500-hour reaction, an acrylonitrile yield of 77.6%, a hydrocyanic acid yield of 3.4% and an acetonitrile yield of 4.1% were calculated, the rest being made up of combustion products of propylene, which is converted for 98.2%. The ammonia conversion is thorough. Neither carboxylic by-products, nor losses of elements of the activated part of the catalyst due to reduction were found.

We claim:

1. The process for the preparation of acrylonitrile or methacrylonitrile from propene or, respectively, isobutene, by reaction, in the gas phase, with ammonia and oxygen, in the presence of a solid catalyst system, at a temperature between 350° and 550°C, said process being characterized in that the catalyst system consists of the elements tellurium, cerium and molybdenum, and of at least one element selected from the group consisting of iron, chromium and aluminum, all of said elements being chemically combined with oxygen, and the various elements being present in the atomic ratios defined by the following empirical formula:

$A_xC_yTe_vMo_{12}O_z$ where A is at least one element selected from the group consisting of iron, chromium and aluminum, wherein:
  $x = 0.3 - 4$;
  $y = 1 - 10$;
  $v = 1 - 10$; and
  $z$ is a number indicating the amount of oxygen bound to the other elements and corresponding to the oxidation state in which they exist in the catalyst, said catalyst being obtained by mixing compounds of Te, Ce and Mo and of at least one element selected from the group consisting of Fe, Cr and Al in an aqueous medium, and then drying the mixture and heating it in the presence of air at a temperature ranging from 450° to 700°C.

2. The process of claim 1 wherein the catalyst is used with a catalyst support.

3. The process of claim 2 wherein the support is silica.

4. The process of claim 1 wherein the catalyst is used in the form of a fixed or fluidized catalyst bed.

* * * * *

UNITED STATES PATENT OFFICE
CERTIFICATE OF CORRECTION

Patent No. 3,969,390　　　　　　　Dated July 13, 1976

Inventor(s) Franco FALETTI et al

It is certified that error appears in the above-identified patent and that said Letters Patent are hereby corrected as shown below:

Col. 1, line 24, "catalyst" should be ---catalytic---.

Col. 1, line 44, "furhter" should be ---further---.

Col. 2, line 57, "sacle" should be ---scale---.

Col. 3, line 4 , "throughly" should be ---thoroughly---.

Col. 5, line 37, "dired" should be ---dried---.

Col. 6, line 48, insert "said" before "catalyst".

Col. 7, line 29, "comprosed" should be ---composed---.

Signed and Sealed this

Seventh Day of March 1978

[SEAL]

Attest:

RUTH C. MASON　　　　　　　LUTRELLE F. PARKER
Attesting Officer　　　　Acting Commissioner of Patents and Trademarks